United States Patent [19]

Jacob

[11] Patent Number: 5,569,679
[45] Date of Patent: Oct. 29, 1996

[54] PHARMACOLOGIC MANAGEMENT OF SNORING

[75] Inventor: Stanley W. Jacob, Portland, Oreg.

[73] Assignee: Russell A. Krueger Pharmaceuticals, Inc., Portland, Oreg.

[21] Appl. No.: 366,666

[22] Filed: Dec. 30, 1994

[51] Int. Cl.$^6$ .................. A61K 31/10; A61K 31/045
[52] U.S. Cl. ................. 514/711; 514/724; 514/923
[58] Field of Search ..................... 514/711, 923

[56] References Cited

U.S. PATENT DOCUMENTS

| | | | |
|---|---|---|---|
| 4,477,469 | 10/1984 | Herschler | 514/588 |
| 4,863,748 | 9/1989 | Herschler | 426/72 |

OTHER PUBLICATIONS

"Y Snore Anti–Snoring Nose Drops" Product, Manufactured By Datong Health Care, China.

*Primary Examiner*—John W. Rollins
*Attorney, Agent, or Firm*—Timothy J. Martin

[57] ABSTRACT

A method of pharmaceutically managing snoring is provided by the instillation intranasally of a solution containing 1–20% methylsulfonylmethane by weight dissolved in water so as to saturate the nasal mucous membranes. Preferably, the solution has between 10%–16% by weight methysulfonylmethane. The solution may be buffered, and/or a mild analgesic may be included. The method prefers that instillation occur as close to the sleep event as possible, and it should be at least within one hour before a person retires for sleep. The solution may be introduced by spray or dropwise, and a product packaging the solution in a suitable container is described.

18 Claims, 1 Drawing Sheet

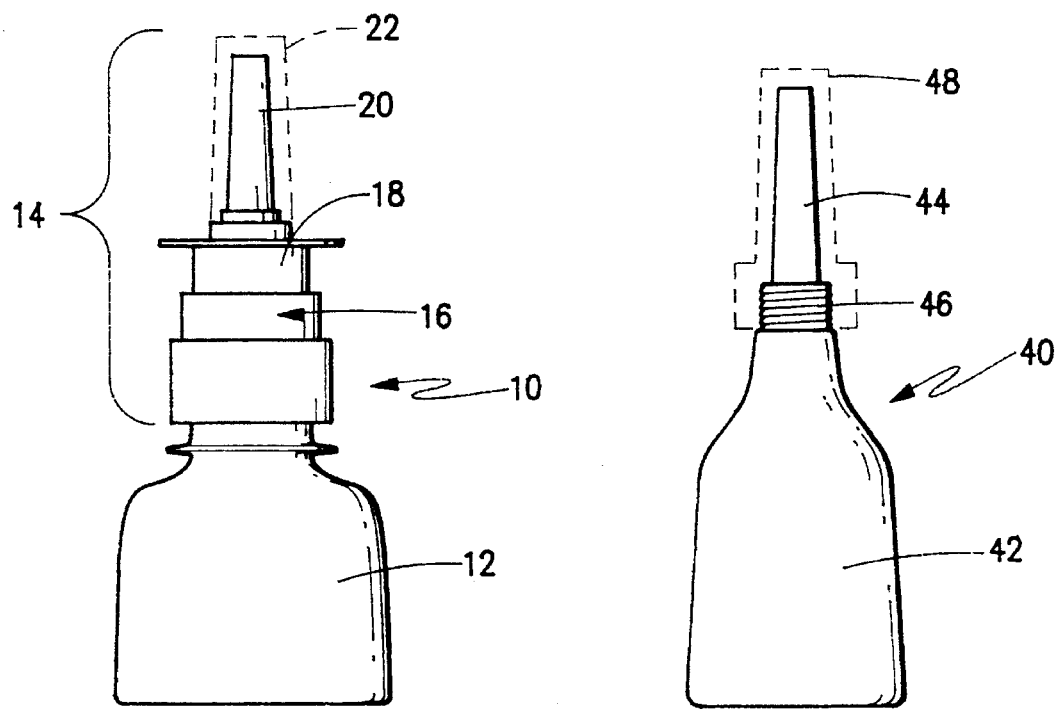
Fig.1 (PRIOR ART)
Fig.2 (PRIOR ART)
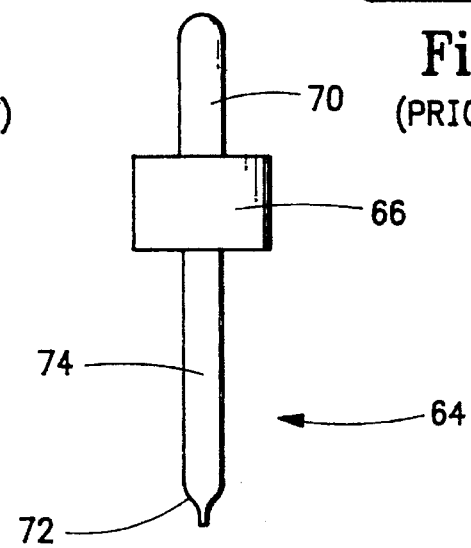
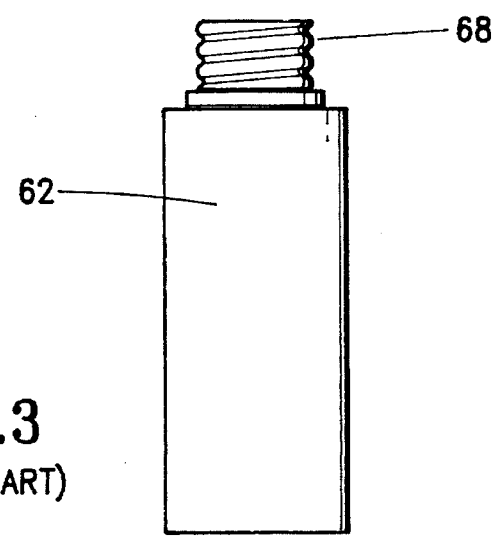
Fig.3 (PRIOR ART)

PHARMACOLOGIC MANAGEMENT OF SNORING

FIELD OF THE INVENTION

The present invention broadly concerns the management of snoring by reducing the incidence or magnitude thereof. More particularly, however, the present invention is directed to reducing or eliminating snoring by pharmacologic means. This invention directly concerns the method of managing snoring by the instillation of pharmacologic solutions into the nasal passageway.

BACKGROUND OF THE INVENTION

Snoring is an inspiratory sound which arises during a person's sleep. Snoring is believed to be generally caused by the narrowing of the nasopharyngeal airway such that turbulent airflow during relaxed breathing vibrates the soft parts of the oropharyngeal passage, such as the soft pallet, the posterior faucial pillars of the tonsils and the uvula. Many causes for the narrowing of the nasal pharyngeal airway, especially during sleep, exist, as noted below.

Snoring afflicts a large segment of the population, and is a condition affecting both sexes of all ages. During wakefulness, a person is typically able to consciously maintain the nasal pharyngeal passageway in an open condition; however, with the onset of sleep, relaxation allows the nasopharyngeal passageway to restrict, and snoring results. It has been estimated that up to 45% of all adults snore occasionally with about 25% being habitual snorers. Snoring increases with age, and it has been observed that about 50% of men and 40% of women are habitual snorers by the age of 60. Lugaresi et al, "Snoring: Pathogenic, Clinical and Therapeutic Aspects", Reported in *Principles and Practice of Sleep Medicine* (Kryger et al, Editors 1989) at pp. 494–500.

A restricted nasopharyngeal passageway can occur anatomically. For example, in children, this often is caused by obstruction due to enlarged tonsils or adenoids. In adults, it is not unusual for the narrowing to be caused by obesity. Further anatomical narrowing can be simple a matter of genetics with some persons being predisposed towards a smaller nasopharyngeal cross-section. A reduced nasopharyngeal passageway may also be caused by a lack of muscle tone. Other anatomical conditions contributing to the narrowing of the nasal pharyngeal passageway include choanal atresia, chrono polyp, nasal septal deviation, nasal pharyngeal cyst, macroglossia, retrognathia and micrognathia, but these less common. Leung et al, "The ABZzzz's of Snoring", *Post Graduate Medicine* (Sep. 1, 1992).

Snoring may also be exacerbated by consuming either alcohol or drugs (such as tranquilizers, sleeping pills and antihistamines) prior to bedtime. Smoking can contribute to the incidence of snoring since cigarettes may irritate the mucus membranes of the upper airway causing swelling and increased mucus production.

Heretofore, it has been reported that there is no indication of pharmacologic management of snoring. Douglas, "The Sleep Apnoea/Hypopnoea Syndrome and Snoring", *DMJ*, Volume 306 (1993); Leung et al, "The ABZzzz's of Snoring", *Post Graduate Medicine* (Sep. 1, 1992). However, numerous management techniques have been described, depending upon the perceived cause of snoring. None of these treatments have proved completely adequate. Where snoring is caused or exacerbated by nasal allergy or an upper respiratory track infection, these conditions may be treated pharmacologically, but, as noted above, this is not deemed to be a pharmacologic management of the overall snoring condition.

A basic treatment simply involves having the patient sleep in the prone position or on his/her side. Sometimes this is stimulated by sewing a marble or other object into the back of the snorer's clothes. Where the patient is obese, treatment may be a program of weight loss. Along with these treatments, of course, is the recommendation that the patient avoid use of drugs, cigarettes or alcohol prior to bedtime so as to retard the loss of oropharyngeal muscle tone.

Snoring can sometimes be managed by the use of an appliance. One example is a custom-made mouth-piece constructed to move the snorer's lower jaw forwardly, thus opening the airway. Another example is the use of a positive pressure generator and face mask. These machines pump air through a hose and nose/mouth face mask to keep air passages clear. Use of each of thee devices, however, can cause the subject to have less restful sleep.

Another option for treating snoring is found with surgical techniques. In children whose snoring is caused by an enlarge adenoids, and adenoidtotomy is sometimes prescribed. Where tonsils are also enlarged, a tonsillectomy often accompanies surgery to the adenoids. In adults, uvulopalatopharyngoplasty may be recommended for habitual or heavy snorers. Here, the surgeon resects the uvula, the distal portion of the soft pallet, the anterior tonsillar pillars and the redundant lateral pharyngeal wall mucosa. The purpose of such surgery, of course, is to increase the size of the air passageway thereby allowing unobstructed movement of air through the pharynx. Rates of success of the uvulopalatopharyngoplasty are uncertain, with improvement reported to be in a range from 15% to 65%. Douglas, "The Sleep Apnoea/Hypopnoea Syndrome And Snoring", *British Medical Journal,* 1993, Vol. 306:1057–60. In some instances, surgical repair of a deviated nasal septum has been shown to improve snoring.

Snoring, therefore, remains a serious problem for a large segment of the population. Not only is it a nuisance, but can itself indicate a more serious condition and, due to exhaustion resulting from lack of sleep, can cause other problems. For example, an association between snoring and hypertension has been found, and cardiac arrhythmia has been reported during sleep apnea attacks. Snoring patients with decreased pulmonary function have been shown to suffer from severe apnea. Not only is the risk of cessation of breathing a danger for snoring, lack of oxygen due to an obstructed nasopharyngeal passageway deprives the body of sufficient oxygen so that an oxygen desaturation arises. Lack of oxygen may cause the brain to rouse the sleeper just enough to take a breath without fully awaking. Since this may happen hundreds of times a night, the snorer does not get sufficient sleep. Moreover, being aroused from deep REM sleep on a repetitive basis may increase heart rate and blood pressure. Thus, snoring may increase the risk of heart attack and stroke, as noted above. Further, due to narcolepsy resulting from exhaustion can cause a lack of attention for the snorer during waking hours thus reducing productivity and even causing dangerous situations should the exhausted snorer operate machinery or vehicles.

Accordingly, there has been a long felt need for improved management techniques to reduce or eliminate snoring. Specifically, a long felt need has existed for pharmacologic methodology in treating snoring which is simple and safe to administer. The present invention is directed to such pharmacological management technique.

SUMMARY OF THE INVENTION

It is an object of the present invention to provide a new and useful method for the pharmacologic management of snoring.

Another object of the present invention is to provide a safe and relatively effective pharmacologic treatment which can be self-administered by a snorer prior to retiring for sleep.

Yet another object of the present invention is to provide an inexpensive pharmacologic method to reduce the incidence and/or magnitude of snoring that is safe and relatively effective for use.

Still a further object of the present invention is to provide a method directed to the installation of methysulfonyl-methane (MSM) into the nasal passageway as a management technique for snoring.

Still another object of the present invention is to provide a product in the form of a dispenser containing a methysulfonylmethane composition which may be instilled by an applicator into the nasal passageway as a method of reducing or eliminating the instance of snoring.

According to the present invention, then, a method for managing snoring is provided by the step of instilling a solution intranasally within a patient's nasal cavity wherein the solution includes a carrier solvent containing an effective amount of methylsulfonylmethane as a solute therein. Preferably, the solvent is water, and the methysulfonylmethane is dissolved therein within a range of 1% and 20% by weight, inclusively. The solvent may also be water and phosphate buffered saline mixed in equal ratios.

Preferably, approximately 10% to 16% by weight of methysulfonylmethane is used, and the solution is instilled into the nasal passageway as a spray or drop-wise. The solution may contain a mild analgesic composition, if desired. Examples of such analgesic compositions include: menthol, procaine, xylocaine and the like. Regardless of the mechanism by which the solution is instilled, it is preferred that the solution be instilled within one hour, and preferably within an interval no more than ten minutes before the patient retires for sleep. Moreover, an amount of solution should be instilled of a sufficient quantity to saturate the patient's nasal mucus membranes, typically on the order of 0.5 ml to 1.0 ml per nostril.

The present invention also includes a product which is adapted for use in treating snoring. Here, the product is a solution containing a solvent for methysulfonylmethane and an amount of methysulfonylmethane dissolved therein. The solution is then packaged in a container. The container includes an applicator associated therewith for instilling the solution internasally within a patient's nasal cavity. In one embodiment, the applicator is a dropper. In another embodiment, the applicator is an aerosol nozzle, either providing a measured or unmeasured dosage of the solution described above.

These and other objects of the present invention will become more readily appreciated and understood from a consideration of the following detailed description of the preferred embodiments when taken together with the accompanying drawings, in which:

BRIEF DESCRIPTION OF THE DRAWINGS

FIG. 1 is a side view in elevation of a first exemplary embodiment of a prior art container suitable for use with the present invention;

FIG. 2 is a side view in elevation of a second exemplary embodiment of a prior art container suitable for use with the present invention; and FIG. 3 is a side view in elevation of a third exemplary embodiment of a prior art container and dropper suitable for use with the present invention;

DETAILED DESCRIPTION OF THE EXEMPLARY EMBODIMENTS

The present invention concerns the pharmacologic management of snoring by the instillation into the nasal passageway of a pharmacologic composition containing an effective amount of dimethysulfone ($DMSO_2$), also known as methysulfonylmethane (MSM). Heretofore, relief of the snoring condition has not readily responded to pharmacologic treatment. It has been surprisingly found that methysulfonylmethane dissolved in a pharmaceutically acceptable solvent when administered to saturate the mucous membranes of the nasal passageways acts to reduce the instance of snoring for a time interval for approximately 8–12 hours.

According to the present invention, then, a method of managing snoring has been developed which comprises the step of instilling a solution internasally within a patient's nasal cavity wherein the solution includes a carrier solvent containing an effective amount of methylsulfonylmethane as a solute therein. Preferably, the solvent is distilled water, although any solvent which may dissolve the effective amount of methylsulfonylmethane while at the same time being pharmaceutically acceptable for instillation into the nasal cavity is suitable. Water and phosphate buffered saline, mixed in a 1:1 ratio (equal proportions) by volume may serve as the solvent as many patients prefer this mixture to plain distilled water. While any suitable amount of methysulfonylmethane may be dissolved in the solvent up to the saturation level, where the solvent is water, it is preferred that the solution contain between 1% and 20%, by weight, inclusively, of methylsulfonylmethane. An analgesic compound may be included within the solution in order to minimize any unpleasant irritation. Such analgesic compound may be menthol or any pharmaceutically acceptable local analgesic composition such as procaine, xylocaine and the like, usually at dosages less than ½% by weight. Where menthol is used, it is preferred that the amount of menthol be 0.25% by weight.

The initial experiments to determine effectiveness of the instillation of methylsulfonylmethane as a snoring reduction agent was carried out with an initial sampling of 15 individuals. The empirical data collected for the initial experiment is summarized in the following Table I.

TABLE I

| Subject | Sex | Age | % MSM (by weight) | Results |
|---|---|---|---|---|
| AO | M | 56 | 16 | R |
| US1 | M | 62 | 16 | R |
| MD | F | 50 | 16 | R |
| GC1 | F | 56 | 15 | R |
| PH | M | 61 | 15 | R |
| DM | M | 62 | 15 | R |
| GC2 | M | 72 | 14 | NR |
| EC | M | 76 | 14 | R |
| DR | M | 83 | 14 | R |
| RB | M | 56 | 13 | R |
| MS | F | 69 | 13 | R |
| AD | M | 50 | 13 | NR |
| SJ | M | 70 | 12 | R |
| US2 | F | 76 | 12 | R |
| RP | M | 60 | 11 | NR |

R = Relief
NR = No Result

In each of the above cases, the subject was instructed to instill approximately 0.5 to 1.0 milliliters (8–16 drops) of the solution containing the methylsulfonylmethane approximately ten minutes to 1 hour prior to retiring for sleep. The observation of the presence or absence of snoring was made by the subject's mate. The observing party was not told that the subject was employing internasal methylsulfonylmethane. As noted in Table I, 80% of the subject's mates reported the lessening or absence of snoring while 20% reported no result from the internasal administration of the methylsulfonylmethane.

A second sampling of subjects was undertaken wherein the weight percentage of methylsulfonylmethane in water was varied at 10% and below. Results of this study is summarized in the following Table II:

TABLE II

| Subject | Sex | Age | % MSM (by weight) | Results |
| --- | --- | --- | --- | --- |
| SC | F | 54 | 10% | R |
| JB1 | M | 34 | 10% | R |
| TC | F | 33 | 9% | R |
| JP | F | 55 | 9% | R |
| WW | M | 74 | 8% | NR |
| CM | F | 54 | 7% | R |
| RB2 | M | 62 | 6% | R |
| HP | M | 42 | 6% | R |
| WS | M | 65 | 6% | R |
| JM | F | 49 | 5% | R |
| KS | M | 40 | 4% | R |
| JS | M | 60 | 3% | R |
| SG | M | 52 | 2% | R |
| RH | M | 59 | 1% | R |
| JB2 | M | 60 | 1% | NR |

R = Relief
NR = No Result

While Table II demonstrates that relief of snoring occurred at concentrations of as little as 1% methylsulfonylmethane by weight in water, the relief was not reported to be as dramatic as at higher concentrations.

By warming the solution of water and methylsulfonylmethane to no more than about 37° C. (98.6° F.), a greater concentration of methylsulfonylmethane will go into solution. Accordingly, a third sampling of four subjects employed such a warmed solution, and the results are reported in Table III.

TABLE III

| Subject | Sex | Age | % MSM (by weight) | Results |
| --- | --- | --- | --- | --- |
| JB2 | M | 60 | 20% | R |
| EL | M | 39 | 20% | R |
| RF | M | 40 | 19% | R |
| LW | M | 52 | 18% | R |

Here, it may be noted that subject JB2 responded positively to 20% by weight methylsulfonylmethane whereas earlier the subject had shown no result to 1% methylsulfonylmethane.

From the data derived from these experiments, as tabulated in Tables I–III, it can be generally surmised that concentrations within a range of 1%–20% methylsulfonylmethane by weight in water are effective. Observations indicate that the higher concentrations within this range are the most effective. However, due to the solubility of methylsulfonylmethane in water, the best range for a useful method and product that avoids the need of warming the solution is in the range of 10%–16% methylsulfonylmethane by weight.

In order to determine whether the mere introduction of fluid against the nasal membranes might have ameliorated the snoring of the subject, a saline solution rather than the methylsulfonylmethane solution was substituted after a period of time for the first five subjects listed in Table I. Whereas relief had been present in all five subjects while receiving the MSM/$H_2O$ solution, when that solution was replaced with the saline solution, snoring returned for all subjects on the initial night of the substitution. This indicates that it is the saturation of the nasal membrane with the MSM/$H_2O$ solution that caused the desired effect. Moreover, it was been observed that the positive effect of reduced snoring was achieved the closer in time to retiring for sleep that instillation of the solution occurs. Further, it has been observed that saturation of the nasal membranes achieves the maximum effect. Several subjects reported that good results occurred where the solution was re-instilled during the night were they awakened from slumber.

In certain instances, some of the subjects in Table I observed minor irritation upon introduction of the methylsulfonylmethane solution into the nasal passageway. In order to minimize any irritation, a mild analgesic compound was included in the solution. In one example, approximately 0.25% by weight menthol was placed in solution. Of the patients who had experienced irritation, about ⅓ indicated a preference for the menthol solution while ⅔ preferred the solution without the menthol. Alternatively, a majority of the subjects who received a solution made of equal proportions of water and phosphate buffered saline indicated a preference for the mixture over the simple water solution except for the inconvenience of refrigeration needed to prevent deterioration of the buffered phosphate. Refrigeration also reduces the amount of methylsulfonylmethane which will remain in the solution.

With reference to FIGS. 1–3, it should be appreciated that the solution according to the present invention may be administered through a variety of known techniques, and the present invention is also directed to a product that may be used in treating snoring. Here, the product may be in the form of a solution including a solvent for methylsulfonylmethane and an amount of methylsulfonylmethane dissolved therein. This solution is then packaged in a container with the container included an applicator associated therewith for instilling the solution internasally within a subject or patients nasal cavity.

With reference to FIG. 1, a prior art container is shown which is of the type used to instill a metered quantity of solution into the internasal passageway. In FIG. 1, container 10 includes a bottle 12 for holding the methylsulfonylmethane solution. Applicator 14 includes a metering pump 16 activated by a plunger 18. Upon depressing plunger 18 toward bottle 12, a metered quantity of the solution in bottle 12 is ejected through nozzle 20 which is placed in the nostril. When not in use, container 10 is enclosed by means cap 22 (shown in phantom). As noted, the container 10 is of a type known in the prior art for administering a selected metered dosage.

A second prior art container is shown in FIG. 2. Here, container 40 includes a plastic squeeze bottle 42 adapted to hold the fluid to be dispensed. Plastic squeeze bottle 42 communicates with a nozzle 44 that is threaded at 46 to receive a cap 48 (shown in phantom). Here, bottle 42 may be held upright with nozzle 44 positioned in the nostril. Upon squeezing, a mist of solution from bottle 42 is ejected through nozzle 44. Alternatively, bottle 42 may be inverted with nozzle 44 in the nostril and the solution administered drop-wise.

In FIG. 3, a standard eye dropper-type container 60 is shown which includes a bottle 62 adapted to receive the fluid. Eye dropper 64 is received in bottle 62 and is threadably mounted thereto by cap 66 mounted on threaded neck 68. Eye dropper 64 includes a flexible bulb 70 which may be compressed to remove air therefrom. By immersing tip 72 of pipette portion 74 in fluid, the release of pressure on bulb 70 causes an amount of solution to be drawn into pipette 74. Pipette 74 may then be placed into the nostril and the solution administered in drop-wise manner.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. A method of managing snoring comprising the step of instilling a solution intranasally within a subject's nasal cavity wherein said solution includes a carrier solvent containing an effective amount of methylsulfonylmethane as a solute therein.

2. The method according to claim 1 wherein said solution also includes an analgesic compound dissolved therein.

3. The method according to claim 2 wherein said analgesic compound is menthol.

4. The method according to claim 1 wherein said solvent is water.

5. The method of claim 1 wherein said solvent is water and phosphate buffered saline mixed in a ratio of 1:1 by volume.

6. The method according to claim 4 wherein the amount of methylsulfonylmethane is between one percent (1%) and twenty percent (20%) by weight, inclusively.

7. The method according to claim 4 wherein the amount of methysulfonylmethane is between ten percent (10%) and sixteen percent (16%) by weight, inclusively.

8. The method according to claim 1 wherein the solution is instilled as spray.

9. The method according to claim 1 wherein the solution is instilled drop-wise.

10. The method according to claim 1 wherein the solution is instilled within one hour before the subject retires for sleep.

11. The method according to claim 10 wherein the solution is instilled one half hour or less before the subject retires for sleep.

12. The method according to claim 1 wherein said solution is instilled in a sufficient quantity to saturate the patient's nasal mucous membrane.

13. A product adapted for use in treating snoring, comprising:

(a) a solution including a solvent for methylsulfonylmethane, an analgesic compound dissolved therein and an amount of methylsulfonylmethane between one percent (1%) and twenty percent (20%), inclusively, by weight dissolved therein; and (b) a container for said solution, said container including applicator means associated therewith for instilling said solution intranasally within a patient's nasal cavity.

14. A product according to claim 13 wherein said applicator means is a dropper.

15. A product according to claim 13 wherein said applicator means is an aerosol nozzle.

16. A product according to claim 13 wherein said solvent is water.

17. A product according to claim 13 wherein said analgesic compound is menthol.

18. A product according to claim 13 wherein said solvent is water and phosphate buffered saline mixed in a ratio of 1:1 by volume.

* * * * *